United States Patent
Nutt et al.

(10) Patent No.: US 12,235,250 B2
(45) Date of Patent: Feb. 25, 2025

(54) RADIOPHARMACEUTICAL PRODUCTION SYSTEM AND QUALITY CONTROL SYSTEM UTILIZING HIGH PERFORMANCE LIQUID CHROMATOGRAPHY

(75) Inventors: Ronald Nutt, Friendsville, TN (US); Anthony M. Giamis, Green Oaks, IL (US); Aaron McFarland, Knoxville, TN (US)

(73) Assignee: Best ABT, Inc., Springfield, VA (US)

( * ) Notice: Subject to any disclaimer, the term of this patent is extended or adjusted under 35 U.S.C. 154(b) by 0 days.

(21) Appl. No.: 13/446,334

(22) Filed: Apr. 13, 2012

(65) Prior Publication Data

US 2013/0130309 A1 May 23, 2013

Related U.S. Application Data

(63) Continuation-in-part of application No. 12/565,544, filed on Sep. 23, 2009, now Pat. No. 8,333,952, and a continuation-in-part of application No. 12/565,552, filed on Sep. 23, 2009, now abandoned.

(51) Int. Cl.
| | |
|---|---|
| *G01N 30/74* | (2006.01) |
| *A61K 51/04* | (2006.01) |
| *B01J 19/00* | (2006.01) |
| *G01N 30/88* | (2006.01) |
| *G01N 33/60* | (2006.01) |
| *G01N 30/00* | (2006.01) |

(52) U.S. Cl.
CPC ......... *G01N 30/74* (2013.01); *A61K 51/0491* (2013.01); *B01J 19/0093* (2013.01); *G01N 30/88* (2013.01); *G01N 33/60* (2013.01); *B01J 2219/00788* (2013.01); *B01J 2219/00873* (2013.01); *B01J 2219/00891* (2013.01); *B01J 2219/00905* (2013.01); *G01N 2030/77* (2013.01); *G01N 2030/8872* (2013.01)

(58) Field of Classification Search
CPC ............................... G01N 30/74; G01N 33/60
USPC ...................................................... 424/1.89
See application file for complete search history.

(56) References Cited

U.S. PATENT DOCUMENTS

| | | | | |
|---|---|---|---|---|
| 6,033,546 A | * | 3/2000 | Ramsey | ........................ 204/603 |
| 7,329,538 B2 | * | 2/2008 | Wainwright et al. | ...... 435/288.7 |
| 8,333,952 B2 | | 12/2012 | Nutt et al. | |
| 8,937,287 B2 | | 1/2015 | Giamis | |
| 2005/0232861 A1 | | 10/2005 | Buchanan et al. | |
| 2008/0064110 A1 | * | 3/2008 | Elizarov et al. | ................. 436/50 |
| 2008/0067413 A1 | | 3/2008 | Nutt | |
| 2008/0226552 A1 | | 3/2008 | Powell et al. | |
| 2008/0233018 A1 | | 9/2008 | van Dam et al. | |
| 2009/0036668 A1 | | 2/2009 | Elizarov et al. | |
| 2010/0145630 A1 | | 6/2010 | Ball et al. | |
| 2011/0070160 A1 | | 3/2011 | Nutt et al. | |
| 2011/0178359 A1 | * | 7/2011 | Hirschman | ............ G16H 20/17 600/4 |
| 2015/0157743 A1 | | 6/2015 | McFarland et al. | |
| 2015/0160171 A1 | | 6/2015 | Anzellotti et al. | |
| 2015/0238918 A1 | | 8/2015 | Khachaturian et al. | |

FOREIGN PATENT DOCUMENTS

| | | | |
|---|---|---|---|
| WO | 2012024663 | 2/2012 | |
| WO | WO-2012024663 A1 * | 2/2012 | ............. G01N 21/31 |

OTHER PUBLICATIONS

Machulla et al. J. Radioanal. Chem. 1976, 381-400.*
Anal. Chrom. Tech. Radiopharm. Chem. 1986, 125-148.*
Shetty et al. J. Pharm. Exp. Therap. 2008, 727-735.*
Shao et al. App. Radiat. Isot. 2011, 69, 403-409.*
Dolan LC 1985 3(12), 1050-1052. (Year: 1985).*
Crouzel C. et al, Radiopharmaceutical for Positron Emission Tomography, Methodological Aspects, Kluwer Academic Publishers, XP009135416.
9.1 Detectors, James M. Miller: Chromatography-Concepts and Contrasts, 2005, Wiley-Interscience, XP-002708718.
J. Koziorowski et al.; A simple method for the quality control of [18F] FDG; Applied Radiation and Isotopes, www.elsevier.com/locate/apradiso.
Stephen M. Moerlein; Robotic preperation of sodium Acetate C11 Injection for use in clinical PET, Nuclear Medicine and Biology 29 (2002) www.elsevier.com/locate/nucmedbio.
H. Denutte; Remote-controlled, Photosynthetic Preperation of HPLC-Purified [11C] Glucose; Int. J. Appl.Radiat. Isot. vol. 36 No 1. pp 82-84, 1985.
G. Stoecklin; Qaulity Assurance and Qaulity Control of Short-Lived Radiopharmaceuticals for Pet, , Kluwer Academic Publishers, Radiopharamceuticals for Positron Emission.
S Yu, PhD, Review of 18 F-FDG synthesis and qaulity control, Biomedical Imaging and Intervention Journal.
Supp'l European Search Report; European Patent Office; EPO Form 1503; Date Feb. 6, 2017.

* cited by examiner

*Primary Examiner* — Michael G. Hartley
*Assistant Examiner* — Sean R Donohue

(57) ABSTRACT

HPLC-based quality control systems to perform quality control testing on a radiopharmaceutical solution shortly after synthesis. An HPLC-based quality control system makes efficient use of sample volume and is compatible with a variety of radioisotopes and radiopharmaceutical compounds. In several embodiments, the automated nature of an HPLC-based quality control system allows for quality control tests to be conducted quickly and with minimal impact on user workflow. When used as part of an integrated PET biomarker radiopharmaceutical production system, the present general inventive concept permits a manufacturer to produce product and conduct quality control tests with lower per dose costs.

34 Claims, 5 Drawing Sheets

RADIOPHARMACEUTICAL PRODUCTION SYSTEM AND QUALITY CONTROL SYSTEM UTILIZING HIGH PERFORMANCE LIQUID CHROMATOGRAPHY

CROSS-REFERENCE TO RELATED APPLICATIONS

This application is a continuation-in-part of U.S. patent application Ser. No. 12/565,544, filed Sep. 23, 2009, and a continuation-in-part of U.S. patent application Ser. No. 12/565,552, filed Sep. 23, 2009.

STATEMENT REGARDING FEDERALLY-SPONSORED RESEARCH OR DEVELOPMENT

Not Applicable

BACKGROUND OF THE INVENTION

1. Field of Invention

This invention relates to chemical apparatuses and processes for synthesizing, purifying, and conducting quality control tests on radiopharmaceuticals for use in positron emission tomography (PET). Specifically, the present invention relates to systems for analyzing a liquid sample of PET biomarker.

2. Description of the Related Art

A biomarker is used to interrogate a biological system and can be created by "tagging" or labeling certain molecules, including biomolecules, with a radioisotope. A biomarker that includes a positron-emitting radioisotope is required for positron-emission tomography (PET), a noninvasive diagnostic imaging procedure that is used to assess perfusion or metabolic, biochemical and functional activity in various organ systems of the human body. Because PET is a very sensitive biochemical imaging technology and the early precursors of disease are primarily biochemical in nature, PET can detect many diseases before anatomical changes take place and often before medical symptoms become apparent. PET is similar to other nuclear medicine technologies in which a radiopharmaceutical is injected into a patient to assess metabolic activity in one or more regions of the body. However, PET provides information not available from traditional imaging technologies, such as magnetic resonance imaging (MRI), computed tomography (CT) and ultrasonography, which image the patient's anatomy rather than physiological images. Physiological activity provides a much earlier detection measure for certain forms of disease, cancer in particular, than do anatomical changes over time.

A positron-emitting radioisotope undergoes radioactive decay, whereby its nucleus emits positrons. In human tissue, a positron inevitably travels less than a few millimeters before interacting with an electron, converting the total mass of the positron and the electron into two photons of energy. The photons are displaced at approximately 180 degrees from each other, and can be detected simultaneously as "coincident" photons on opposite sides of the human body. The modern PET scanner detects one or both photons, and computer reconstruction of acquired data permits a visual depiction of the distribution of the isotope, and therefore the tagged molecule, within the organ being imaged.

Most clinically-important positron-emitting radioisotopes are produced in a cyclotron. Cyclotrons operate by accelerating electrically-charged particles along outward, quasi-spherical orbits to a predetermined extraction energy generally on the order of millions of electron volts. The high-energy electrically-charged particles form a continuous beam that travels along a predetermined path and bombards a target. When the bombarding particles interact in the target, a nuclear reaction occurs at a sub-atomic level, resulting in the production of a radioisotope. The radioisotope is then combined chemically with other materials to synthesize a radiochemical or radiopharmaceutical (hereinafter "radiopharmaceutical") suitable for introduction into a human body. The cyclotrons traditionally used to produce radioisotopes for use in PET have been large machines requiring great commitments of physical space and radiation shielding. These requirements, along with considerations of cost, made it unfeasible for individual hospitals and imaging centers to have facilities on site for the production of radiopharmaceuticals for use in PET.

Thus, in current standard practice, radiopharmaceuticals for use in PET are synthesized at centralized production facilities. The radiopharmaceuticals then must be transported to hospitals and imaging centers up to 200 miles away. Due to the relatively short half-lives of the handful of clinically important positron-emitting radioisotopes, it is expected that a large portion of the radioisotopes in a given shipment will decay and cease to be useful during the transport phase. To ensure that a sufficiently large sample of active radiopharmaceutical is present at the time of the application to a patient in a PET procedure, a much larger amount of radiopharmaceutical must be synthesized before transport. This involves the production of radioisotopes and synthesis of radiopharmaceuticals in quantities much larger than one (1) unit dose, with the expectation that many of the active atoms will decay during transport.

The need to transport the radiopharmaceuticals from the production facility to the hospital or imaging center (hereinafter "site of treatment") also dictates the identity of the isotopes selected for PET procedures. Currently, fluorine isotopes, and especially fluorine-18 (or F-18) enjoy the most widespread use. The F-18 radioisotope is commonly synthesized into [$^{18}$F]fluorodeoxyglucose, or [$^{18}$F]FDG, for use in PET. F-18 is widely used mainly because its half-life, which is approximately 110 minutes, allows for sufficient time to transport a useful amount. The current system of centralized production and distribution largely prohibits the use of other potential radioisotopes. In particular, carbon-11 has been used for PET, but its relatively short half-life of 20.5 minutes makes its use difficult if the radiopharmaceutical must be transported any appreciable distance. Similar considerations largely rule out the use of nitrogen-13 (half-life: 10 minutes) and oxygen-15 (half-life: 2.5 minutes).

As with any medical application involving the use of radioactive materials, quality control is important in the synthesis and use of PET biomarker radiopharmaceuticals, both to safeguard the patient and to ensure the effectiveness of the administered radiopharmaceutical. For example, for the synthesis of [$^{18}$F]FDG from mannose triflate, a number of quality control tests exist. The final [$^{18}$F]FDG product should be a clear, transparent solution, free of particulate impurities; therefore, it is important to test the color and clarity of the final radiopharmaceutical solution. The final radiopharmaceutical solution is normally filtered through a sterile filter before administration, and it is advisable to test the integrity of that filter after the synthesized radiopharmaceutical solution has passed through it. The acidity of the final radiopharmaceutical solution must be within acceptable limits (broadly a pH between 4.5 and 7.5 for [$^{18}$F]FDG, although this range may be different depending upon the application and the radiopharmaceutical tracer involved). The final radiopharmaceutical solution should be tested for the presence and levels of volatile organics, such as ethanol or methyl cyanide, that may remain from synthesis process. Likewise, the solution should be tested for the presence of crown ethers or other reagents used in the synthesis process, as the presence of these reagents in the final dose is problematic. Further, the radiochemical purity of the final solution should be tested to ensure that it is sufficiently high for the solution to be useful. Other tests, such as tests of radionuclide purity, tests for the presence of bacterial endotoxins, and tests of the sterility of the synthesis system, are known in the art.

At present, most or all of these tests are performed on each batch of radiopharmaceutical, which will contain several doses. The quality control tests are performed separately by human technicians, and completing all of the tests typically requires between 45 and 60 minutes.

BRIEF SUMMARY OF THE INVENTION

As disclosed herein, in several example embodiments, the present general inventive concept comprises quality control systems incorporating high performance liquid chromatography (HPLC) to perform quality control testing on a radiopharmaceutical solution shortly after synthesis. In several embodiments, an HPLC-based quality control system according to the present general inventive concept makes efficient use of sample volume and is compatible with and able to test a variety of radioisotopes and radiopharmaceutical compounds. In several embodiments, the automated nature of an HPLC-based quality control system according to the present general inventive concept allows for quality control tests to be conducted quickly and with minimal impact on user workflow. Overall, and especially when used as part of an integrated PET biomarker radiopharmaceutical production system as described herein, the present general inventive concept permits a radiopharmaceutical manufacturer to produce product and conduct quality control tests on the product with lower per dose costs.

An accelerator produces per run a maximum quantity of radioisotope that is approximately equal to the quantity of radioisotope required by the microfluidic chemical production module to synthesize a unit dose of biomarker. Chemical synthesis using microreactors or microfluidic chips (or both) is significantly more efficient than chemical synthesis using conventional (macroscale) technology. Percent yields are higher and reaction times are shorter, thereby significantly reducing the quantity of radioisotope required in synthesizing a unit dose of radiopharmaceutical. Accordingly, because the accelerator is for producing per run only such relatively small quantities of radioisotope, the maximum power of the beam generated by the accelerator is approximately two to three orders of magnitude less than that of a conventional particle accelerator. As a direct result of this dramatic reduction in maximum beam power, the accelerator is significantly smaller and lighter than a conventional particle accelerator, has less stringent infrastructure requirements, and requires far less electricity. Additionally, many of the components of the small, low-power accelerator are less expensive than the comparable components of conventional accelerators. Therefore, it is feasible to use the low-power accelerator and accompanying CPM within the grounds of the site of treatment. Because radiopharmaceuticals need not be synthesized at a central location and then transported to distant sites of treatment, less radiopharmaceutical need be produced, and different isotopes, such as carbon-11, may be used if desired.

If the accelerator and CPM are in the basement of the hospital or just across the street from the imaging center, then radiopharmaceuticals for PET can be administered to patients almost immediately after synthesis. However, eliminating or significantly reducing the transportation phase does not eliminate the need to perform quality control tests on the CPM and the resultant radiopharmaceutical solution itself. Still, it is essential to reduce the time required to perform these quality control tests in order to take advantage of the shortened time between synthesis and administration. The traditional 45 to 60 minutes required for quality control tests on radiopharmaceuticals produced in macro scale is clearly inadequate. Further, since the accelerator and the CPM are producing a radiopharmaceutical solution that is approximately just one (1) unit dose, it is important that the quality control tests not use too much of the radiopharmaceutical solution; after some solution has been sequestered for testing, enough radiopharmaceutical solution must remain to make up an effective unit dose.

In one example embodiment of the present general inventive concept, a high-performance-liquid-chromatography-based quality control testing system to test a sample radiopharmaceutical solution comprises a high performance liquid chromatography column to receive a sample radiopharmaceutical solution. This high performance liquid chromatography column separates molecularly distinct species within the sample radiopharmaceutical solution into a number of separated molecularly distinct species. A refractive index detector measures the amount of each separated molecularly distinct species from said high performance liquid chromatography column, and a radiation detector measures the radioactivity of each separated molecularly distinct species from said high performance liquid chromatography column.

In one example embodiment of the present general inventive concept, an HPLC-based quality control testing system to test a sample radiopharmaceutical solution comprises a valve (in some embodiments, an injection valve) to direct the flow of a sample radiopharmaceutical solution within the system; a sample radiopharmaceutical solution pumping mechanism to direct the sample radiopharmaceutical solution to the valve; a first sample collection vessel to receive a first part of the sample radiopharmaceutical solution from said injection valve, said first sample collection vessel to hold the first part of the sample radiopharmaceutical solution for endotoxicity testing; a fluid loop in fluid communication with said injection valve, said fluid loop to receive a second part of the sample radiopharmaceutical solution; a high performance liquid chromatography column to receive the second part of the sample radiopharmaceutical solution, said high performance liquid chromatography column to separate molecularly distinct species within the second part of the sample radiopharmaceutical solution into a number of separated molecularly distinct species; a refractive index detector to measure the amount of each separated molecularly distinct species from said high performance liquid chromatography column; and a radiation detector to measure the radioactivity of each separated molecularly distinct species from said high performance liquid chromatography column. Often, some embodiments include a high performance liquid chromatography pump to direct a mobile phase solvent to the valve and the HPLC column. In some embodiments, an HPLC-based quality control testing system according to the present general inventive concept also comprises an ultraviolet-light detector or UV/VIS detector to measure the optical qualities of the second part of the sample radiopharmaceutical solution. In some embodiments, the ultraviolet-light detector or UV/VIS detector measures the optical qualities of the second part of the sample radiopharmaceutical solution before the second part of the sample radiopharmaceutical solution enters the high performance liquid chromatography column. Additionally, many embodiments of the present general inventive concept include a pH detector to measure the pH of the sample radiopharmaceutical solution. Further, in some embodiments, the system also includes an automated endotoxin detector to perform endotoxicity testing on the first part of the sample radiopharmaceutical solution held in the first sample collection vessel. In some embodiments, the automated endotoxin detector includes a kinetic hemocyte lysate-based assay.

In some embodiments, an HPLC-based quality control testing system according to the present general inventive concept includes a radiation detector that comprises at least two radiation probes, with a first radiation probe to measure the radioactivity of a part of the sample radiopharmaceutical solution that has not passed through said high performance liquid chromatography column and a second radiation probe to measure the radioactivity of each separated molecularly distinct species from said high performance liquid chromatography column.

In one example embodiment of the present general inventive concept, a method for conducting quality control tests in real time on a radiopharmaceutical comprises: introducing into a reaction vessel a radioisotope and at least one reagent for synthesis of a preselected radiopharmaceutical; reacting said radioisotope and said at least one reagent to produce said preselected radiopharmaceutical in a raw state radiopharmaceutical solution containing undesirable chemical entities; conveying said raw state radiopharmaceutical solution through at least one cleansing step wherein at least one undesirable chemical entity is removed from said radiopharmaceutical solution, whereby said radiopharmaceutical solution is clarified; conveying a portion of said clarified radiopharmaceutical solution to a radiopharmaceutical solution pumping mechanism; pumping said clarified radiopharmaceutical solution to an injection valve, said injection valve to direct the flow of said clarified radiopharmaceutical solution; directing a first aliquot of the clarified radiopharmaceutical solution into a first sample collection vessel, said first sample collection vessel to hold the first aliquot of the clarified radiopharmaceutical solution for measurement of the radioactivity of the clarified radiopharmaceutical solution; directing a second aliquot of the clarified radiopharmaceutical solution into a second sample collection vessel, said second sample collection vessel to hold the second aliquot of the sample radiopharmaceutical solution for endotoxicity testing; directing a third aliquot of the clarified radiopharmaceutical solution into a high performance liquid chromatography column, said high performance liquid chromatography column to separate molecularly distinct species within the third aliquot of the clarified radiopharmaceutical solution into a number of separated molecularly distinct species; measuring the optical qualities of the third aliquot of the sample radiopharmaceutical solution by means of an ultraviolet-light detector; using a refractive index detector to measure the amount of each separated molecularly distinct species from said high performance liquid chromatography column; and measuring the radioactivity of each separated molecularly distinct species from said high performance liquid chromatography column.

In some embodiments, the measurement of the radioactivity of each separated molecularly distinct species from said high performance liquid chromatography column is performed by means of a radiation detector, said radiation detector including at least two radiation probes, said at least two radiation probes including: a first radiation probe to measure the radioactivity of the first aliquot of the sample radiopharmaceutical solution held in said first sample collection vessel; and a second radiation probe to measure the radioactivity of each separated molecularly distinct species from said high performance liquid chromatography column. Further, some embodiments of the method described above include a step of measuring the pH of the clarified radiopharmaceutical solution.

In some embodiments of the present general inventive concept, the radioisotope is selected from the group consisting of carbon-11, nitrogen-13, oxygen-15, and fluorine-18. In some embodiments, the radiopharmaceutical is $[^{18}F]$-2-fluoro-2-deoxy-D-glucose (hereinafter $[^{18}F]FDG$).

The automated nature of an HPLC-based quality control system according to the present general inventive concept allows for quality control tests to be conducted quickly and with minimal impact on user workflow; the automated system relieves a technician from having to perform a number of the quality control tests. When used as part of an integrated PET biomarker radiopharmaceutical production system as described herein, the present general inventive concept permits a radiopharmaceutical manufacturer to produce product and conduct quality control tests on the product with lower per dose costs.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
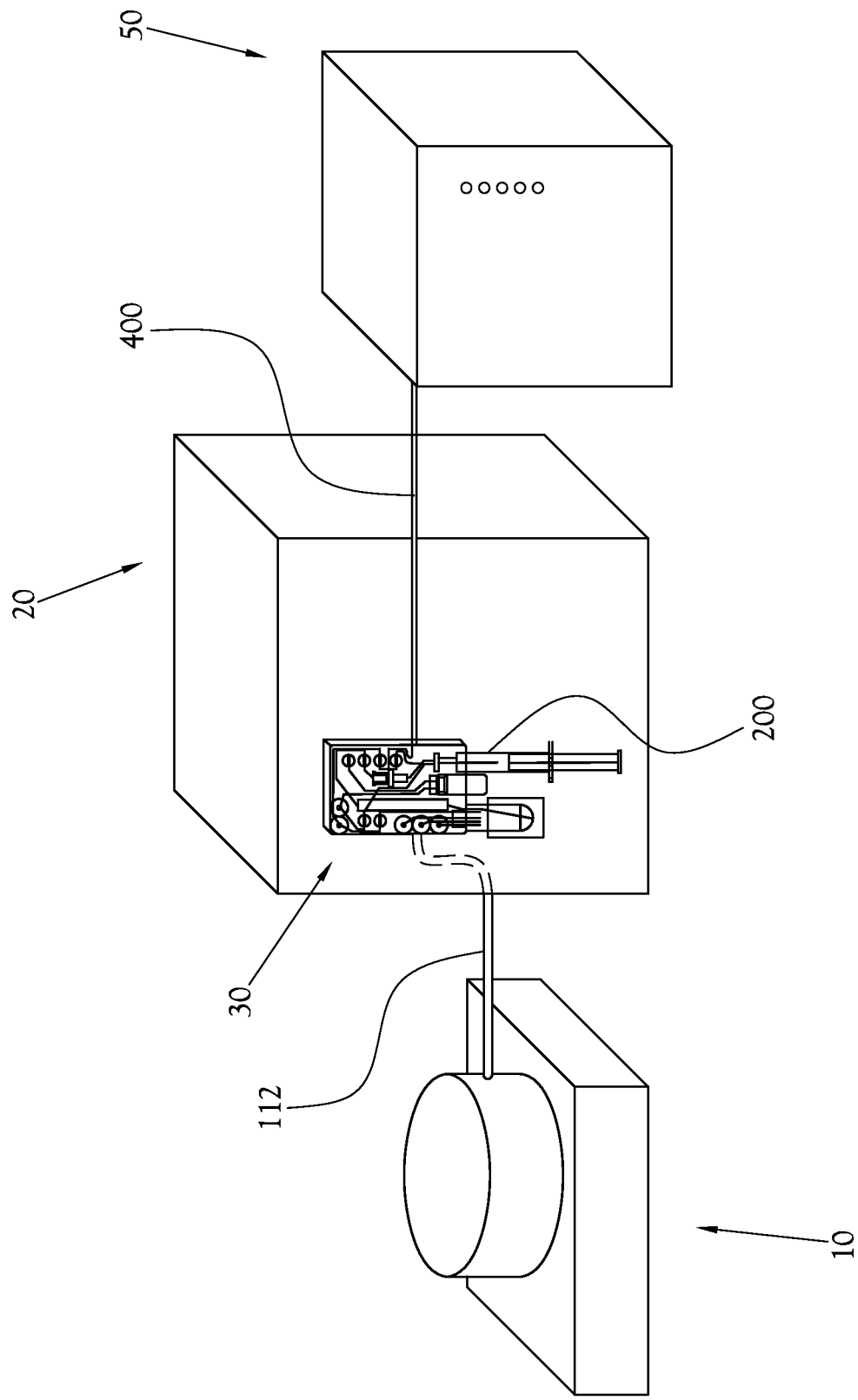
FIG. 1 is an schematic illustration of one example embodiment of the present general inventive concept, showing an overview of a PET biomarker production system, including the accelerator, the chemical production module (CPM), the dose synthesis module (DSM), and the quality control module (QCM)

A chemical production module, dose synthesis module, and HPLC-based quality control module for a PET biomarker radiopharmaceutical production system are described more fully hereinafter. This invention may, however, be embodied in many different forms and should not be construed as limited to the embodiments set forth herein.

Rather, these embodiments are provided to ensure that this disclosure is thorough and complete, and to ensure that it fully conveys the scope of the invention to those skilled in the art.

Thus, in some embodiments of an HPLC-based quality control testing system according to the present general inventive concept, the system comprises an injection valve to direct the flow of a sample radiopharmaceutical solution within the system; a sample radiopharmaceutical solution syringe-pump to direct the sample radiopharmaceutical solution to said injection valve; a high performance liquid chromatography pump to direct a mobile phase solvent to said injection valve; a pH detector to measure the pH of the sample radiopharmaceutical solution; a first sample collection vessel to receive a first aliquot of the sample radiopharmaceutical solution from said injection valve, said first sample collection vessel to hold the first aliquot of the sample radiopharmaceutical solution for measurement of the radioactivity of the sample radiopharmaceutical solution; a second sample collection vessel to receive a second aliquot of the sample radiopharmaceutical solution from said injection valve, said second sample collection vessel to hold the second aliquot of the sample radiopharmaceutical solution for endotoxicity testing; an endotoxin detector to perform endotoxicity testing on the second aliquot of the sample radiopharmaceutical solution held in said second sample collection vessel (in some embodiments, this endotoxin detector includes a kinetic hemocyte lysate-based assay); a fixed-volume fluid loop in fluid communication with said injection valve, said fixed-volume fluid loop to receive a third aliquot of the sample radiopharmaceutical solution from said injection valve; a high performance liquid chromatography column to receive the third aliquot of the sample radiopharmaceutical solution, said high performance liquid chromatography column to separate molecularly distinct species within the third aliquot of the sample radiopharmaceutical solution into a number of separated molecularly distinct species; a refractive index detector to measure the amount of each separated molecularly distinct species from said high performance liquid chromatography column; an ultraviolet-light detector to measure the optical qualities of the third aliquot of the sample radiopharmaceutical solution; and a radiation detector, said radiation detector including at least two radiation probes, said at least two radiation probes including: a first radiation probe to measure the radioactivity of the first aliquot of the sample radiopharmaceutical solution held in said first sample collection vessel; and a second radiation probe to measure the radioactivity of each separated molecularly distinct species from said high performance liquid chromatography column. Further, in some embodiments, the ultraviolet-light detector measures the optical qualities of the third aliquot of the sample radiopharmaceutical solution before the third aliquot of the sample radiopharmaceutical solution enters said high performance liquid chromatography column.

In some of the example embodiments described below, a chemical production module, dose synthesis module, and HPLC-based quality control module operate in conjunction with a complete PET biomarker production system. In one example embodiment of the present general inventive concept, illustrated in FIG. 1, a PET biomarker production system comprises an accelerator 10, which produces the radioisotopes; a chemical production module (or CPM) 20; a dose synthesis module (or DSM) 30; and an HPLC-based quality control module (or QCM) 50. Once the accelerator 10 has produced a radioisotope, the radioisotope travels via a radioisotope delivery tube 112 to the DSM 30 attached to the CPM 20. The CPM 20 holds reagents and solvents that are required during the radiopharmaceutical synthesis process. In the DSM 30, the radiopharmaceutical solution is synthesized from the radioisotope and then purified for testing and administration. Following synthesis and purification, a portion (the "sample portion") of the resultant radiopharmaceutical solution is transported by way of a quality-control transfer line 400 to the QCM 50, and another portion flows into a dose vessel 200. Within the QCM 50, a number of diagnostic instruments perform automated quality control tests on the sample portion.

Figure 2:
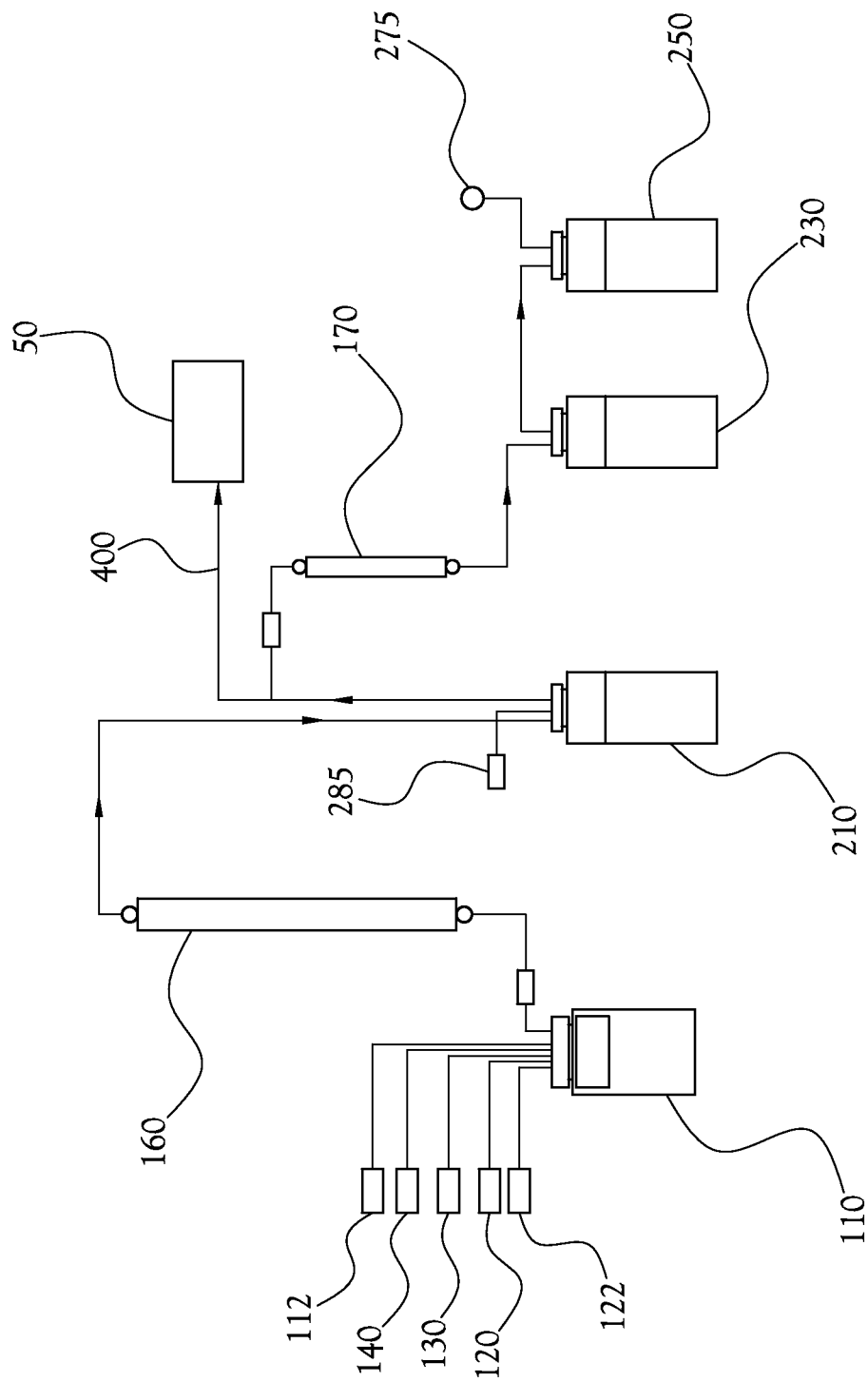
FIG. 2 is a flow diagram illustration of an example embodiment of a DSM according to the present general inventive concept.

FIG. 2 shows a flow diagram of one example embodiment of a dose synthesis module according to the present general inventive concept. In this embodiment, the radioisotope involved is flourine-18 (F-18), produced from the bombardment in a cyclotron of heavy water containing the oxygen-18 isotope. However, the present general inventive concept also embraces radiopharmaceutical synthesis systems generating and using other radioisotopes, including carbon-11, nitrogen-13, and oxygen-15.

As shown in FIG. 2, the radioisotope enters a reaction chamber or reaction vessel 110 from the radioisotope delivery tube 112. At this stage, the radioisotope F-18 is still mixed with quantities of heavy water from the biomarker generator. A number of other reagents and substances are introduced into the reaction vessel 110 by way of several inputs, including, in some embodiments, some or all of the following: a first organic reagent input 120, a second organic reagent input 122, an aqueous input 130, and a gas input. In some embodiments, after the radioisotope enters the reaction vessel 110 from the radioisotope delivery tube 112, a first organic ingredient is introduced to the reaction vessel 110 from the first organic reagent input 120. In some embodiments, the first organic ingredient includes a solution of potassium complexed to 1,10-diaza-4,7,13,16,21,24-hexaoxabicyclo[8.8.8]hexacosane (commonly called Kryptofix 222™, hereinafter "kryptofix") or a similar crown ether. In many embodiments, the potassium-kryptofix complex or similar organometallic complex is carried by acetonitrile as solvent. The potassium activates the F-18 fluoride radioisotope, while the kryptofix binds the potassium atoms and inhibits the formation of a potassium-fluoride complex. Next, the gas input 140 fills the reaction vessel 110 with an inert gas such as dry nitrogen. Then, the mixture in the reaction vessel 110 is heated by to remove residual heavy water by evaporating the azeotropic water/acetonitrile mixture. In some embodiments, a vacuum helps to remove the vaporized water. Next, the second organic input 122 adds a second organic ingredient to the mixture in the reaction vessel 110. In many embodiments, the second organic ingredient is mannose triflate in dry acetonitrile. The solution is then heated at approximately 110 degrees Celsius for approximately two minutes. By this stage, the F-18 has bonded to the mannose to form the immediate precursor for [$^{18}$F]FDG, commonly 18F-fluorodeoxyglucose tetraacetate (FTAG). Next, aqueous acid—in many embodiments, aqueous hydrochloric acid—is introduced through the aqueous input 130. The hydrochloric acid removes the protective acetyl groups on the $^{18}$F-FTAG, leaving $^{18}$F-fludeoxyglucose (i.e. [$^{18}$F]FDG) in what may now be called the synthesized, pre-purified radiopharmaceutical solution.

The [$^{18}$F]FDG having been synthesized, it must be purified before testing and administration. The [$^{18}$F]FDG in solution passes from the reaction vessel 110 through a solid phase extraction column 160. In some embodiments of the present invention, the solid phase extraction column 160 comprises a length filled with an ion exchange resin, a length filled with alumina, and a length filled with carbon-18.

Once the now-purified radiopharmaceutical solution has exited the solid phase extraction column 160, the radiopharmaceutical solution is collected in a product collection vial 210. In many embodiments, the product collection vial 210 includes a vent 285 to allow air or gas to escape the product collection vial 210 as the product collection vial 210 fills with radiopharmaceutical solution. The production collection vial 210 collects all of the purified radiopharmaceutical solution as a single bolus before portions of the purified radiopharmaceutical solution are distributed to other destinations as described infra. From the product collection vial 210, a first portion of the purified radiopharmaceutical solution is directed through a quality-control transfer line 400 to a QCM 50. From the product collection vial 210, a second portion of the purified radiopharmaceutical solution is directed through a sterile filter 170 and through a first post-sterile-filter pathway into a sterility sample vial 230. A first part of the second portion of the purified radiopharmaceutical solution in the sterility sample vial 230 remains in the sterility sample vial 230, and a second part of the second portion of the purified radiopharmaceutical solution in the sterility sample vial 230 travels by way of a second post-sterile-filter pathway into a product injection vial 250. The second part of the second portion of the purified radiopharmaceutical solution collected in the product injection vial 250 is generally the radiopharmaceutical solution that will be administered to one or more patients. In many embodiments, the second part of the second portion of the purified radiopharmaceutical solution collected in the product injection vial 250 constitutes a majority of the radiopharmaceutical solution produced in the synthesis process.

As described, a second portion of the purified radiopharmaceutical solution is directed through a sterile filter 170 before passing through a first post-sterile-filter pathway into the sterility sample vial 230. In some embodiments, the integrity of the filter 170 is tested by passing inert gas through the filter 170 at increasing pressure. A pressure sensor measures the pressure of the inert gas upon the filter 170 and detects whether the filter 170 is still intact. In some embodiments, the filter 170 is expected in to be capable of maintaining integrity under pressures of at least 50 pounds per square inch (psi).

Figure 3:
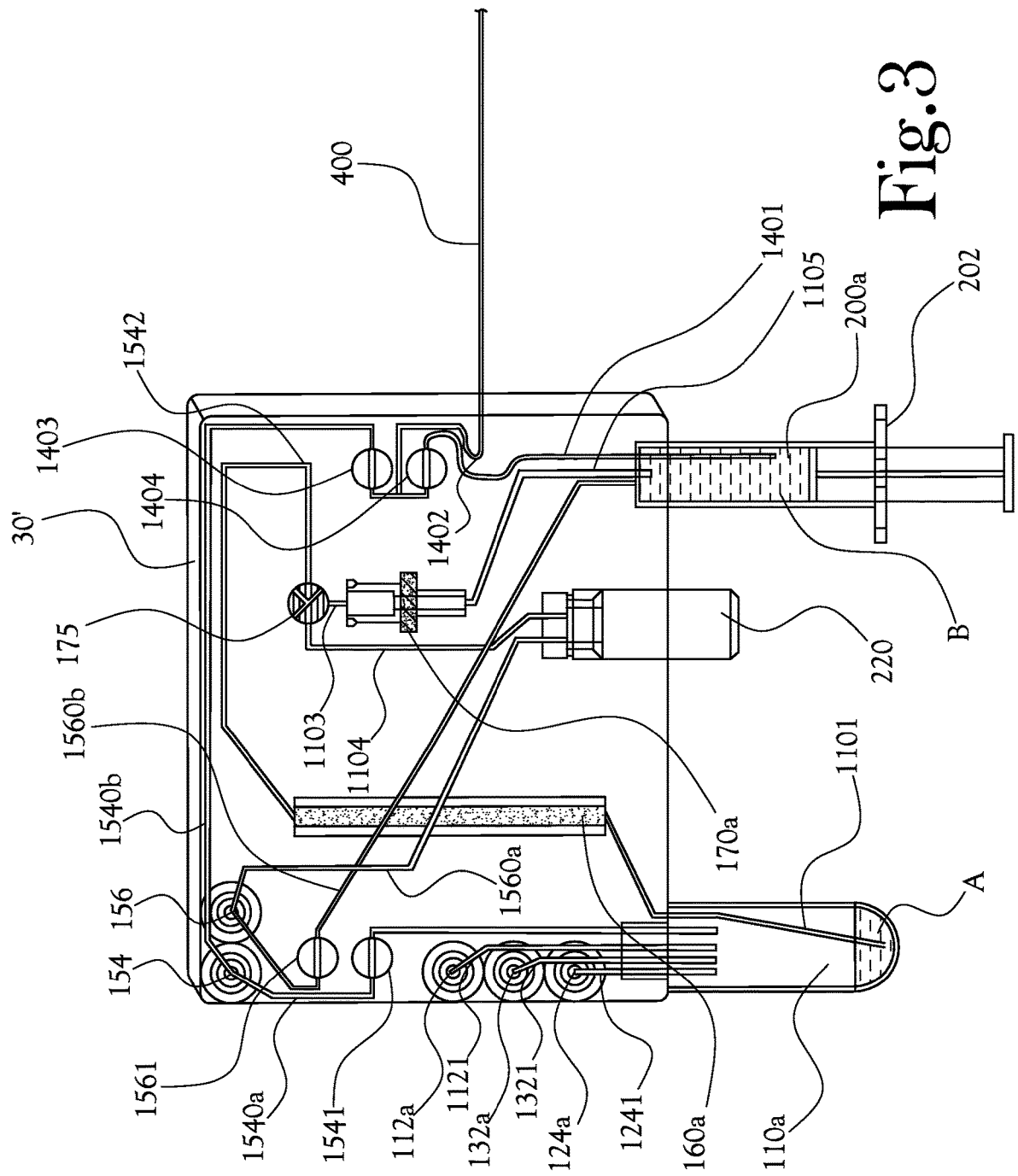
FIG. 3 is a schematic illustration of one example embodiment of the dose synthesis card and the sample card.

FIG. 3 displays a schematic view of one example embodiment of a dose synthesis module (DSM) 30'. The DSM 30' includes a reaction vessel 110a where the radiopharmaceutical solution is synthesized. A radioisotope input 112a introduces the radioisotope F-18 into the reaction vessel 110a through a radioisotope input channel 1121. At this stage, the radioisotope is still mixed with quantities of heavy water from the biomarker generator. Next, an organic input 124a introduces a solution of potassium-kryptofix complex in acetonitrile into the reaction vessel 110a through an organic input channel 1241. A combination nitrogen-input and vacuum 154 pumps nitrogen gas into the reaction vessel 110a through a gas channel 1540a and a valve 1541, which valve is at that time in an open position. The mixture A in the reaction vessel 110a is heated in nitrogen atmosphere to azeotropically remove water from the mixture A, the vaporized water being evacuated through the gas channel 1540a and the vacuum 154. Next, the organic input 124a introduces mannose triflate in dry acetonitrile into the reaction vessel 110a through the organic input channel 1241. The solution is heated at approximately 110 degrees Celsius for approximately two minutes. By this stage, the F-18 has bonded to the mannose to form the immediate precursor for [$^{18}$F]FDG, FTAG. Next, aqueous hydrochloric acid is introduced into the reaction vessel 110a through an aqueous input 132a and an aqueous channel 1321. The hydrochloric acid removes the protective acetyl groups on the intermediate $^{18}$F-FTAG, leaving $^{18}$F-fludeoxyglucose (i.e. [$^{18}$F]FDG).

Having been synthesized, the [$^{18}$F]FDG in solution passes from the reaction vessel 110a through a post-reaction channel 1101 into a solid phase extraction column 160a, where some undesirable substances are removed from the solution, thereby clarifying the radiopharmaceutical solution. In some embodiments of the present invention, the solid phase extraction (SPE) column 160a comprises a length with an ion exchange resin, a length filled with alumina, and a length filled with carbon-18. The radiopharmaceutical passes through the SPE column 160a with a mobile phase that in many embodiments includes acetonitrile from the organic input 124a. As some of the mobile phase and impurities emerge from the SPE column 160a, they pass through a second post-reaction channel 1542 and through a three-way valve 175 and waste channel 1104 into a waste receptacle 220. As the clarified radiopharmaceutical solution emerges from the SPE column 160a, the radiopharmaceutical solution next passes through the second post-reaction channel 1542 and through the three-way valve 175 into a filter channel 1103 and then through a filter 170a. The filter 170a removes other impurities (including particulate impurities), thereby further clarifying the radiopharmaceutical solution. In some embodiments the filter 170a includes a Millipore filter with pores approximately 0.22 micrometers in diameter.

Once the radiopharmaceutical solution has passed through the filter 170a, the clarified radiopharmaceutical solution travels via the post-clarification channel 1105 into the sterile dose administration vessel 200a, which in the illustrated embodiment is incorporated into a syringe 202. In some embodiments, the dose administration vessel is filled beforehand with a mixture of phosphate buffer and saline. As the clarified radiopharmaceutical solution fills the sterile dose administration vessel 200a, a sample portion of the solution B is diverted through an extraction channel 1401 to the quality-control transfer line 400.

After the sample portion of the solution passes into the quality-control transfer line 400, any excess solution remaining in the dose administration vessel 200a is extracted by a vent 156 through a first venting channel 1560b and thence conveyed through an open valve 1561 and through a second venting channel 1560a into the waste receptacle 220. The vacuum 154 evacuates residual solution from the transfer channel 1402 through a now-open valve 1403 and a solution evacuation channel 1540b.

In some embodiments of the present invention, the CPM 20 holds sufficient amounts of reagents and solvents that are required during the radiopharmaceutical synthesis process to carry out multiple runs without reloading. Indeed, in some embodiments the CPM 20 is loaded with reagents and solvents approximately once per month, with that month's supply of reagents and solvents sufficient to produce several dozen or even several hundred doses of radiopharmaceutical. As the reagents and solvents are stored in the CPM 20, it is easier than under previous systems to keep the reagents and solvents sterile and uncontaminated. In some embodiments, a sterile environment is supported and contamination inhibited by discarding each DSM 30 after one run; and thus in these embodiments the DSM 30 is adapted to be disposable.

Thus, each batch of reagents and solvents, loaded periodically into the CPM 20, will supply a batch of multiple doses of radiopharmaceutical, each dose produced in a separate run. Some quality control tests are performed for every dose that is produced, while other quality control tests are performed for every batch of doses. For example, in one embodiment of the present invention, the filter integrity test, the color and clarity test, the acidity test, the volatile organics test, the chemical purity test, and the radiochemical purity test are performed for every dose. On the other hand, some quality control tests need be performed only once or twice per batch, such as the radionuclide purity test (using a radiation probe to measure the half-life of the F-18 in the [$^{18}$F]FDG), the bacterial endotoxin test, and the sterility test. These tests are performed generally on the first and last doses of each batch. Because these per-batch quality control tests are conducted less frequently, they may not be included in the QCM, but rather may be conducted by technicians using separate laboratory equipment.

Figure 4:
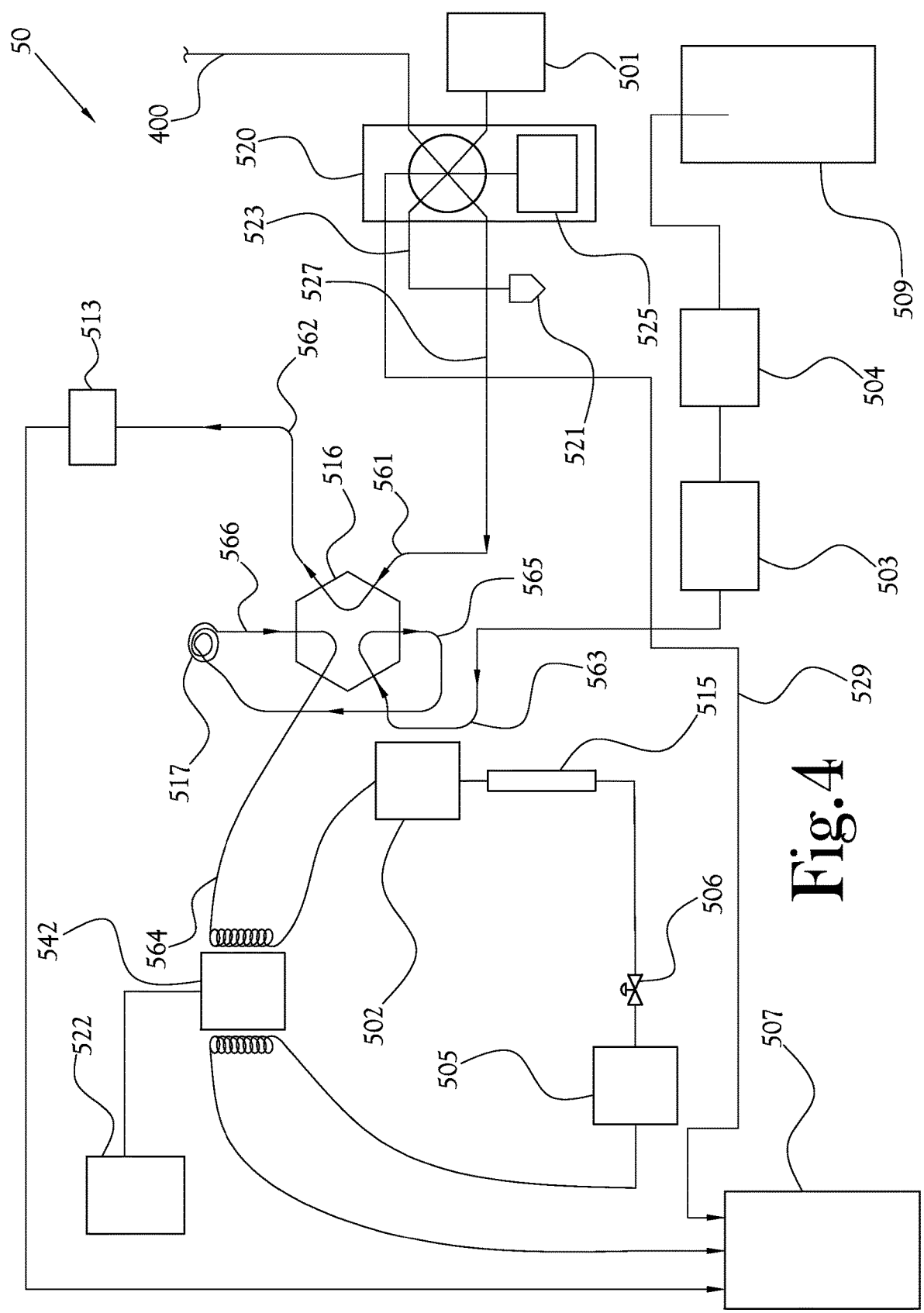
FIG. 4 is a flow diagram illustration of an example embodiment of an HPLC-based QCM according to the present general inventive concept, showing among other items an injection valve for an HPLC-based QCM, showing the injection valve in a first state.

FIG. 4 shows a flow chart illustrating one example embodiment of an HPLC-based QCM 50 according to the present general inventive concept. The example embodiment of an HPLC-based QCM 50 illustrated in FIG. 4 is to test a first portion of purified radiopharmaceutical solution (hereinafter "the sample radiopharmaceutical solution" or simply "sample") from a DSM. As shown in FIG. 4, in some embodiments an HPLC-based QCM 50 according to the present general inventive concept includes an HPLC pump 503, which draws mobile phase solvent from a mobile phase solvent reservoir 509 and through a degasser 504; a syringe-pump assembly 520 to load into the HPLC-based QCM 50 the sample radiopharmaceutical solution from a quality-control transfer line 400; an HPLC column 515; an injection valve 516; and fixed volume fluid loop 517. In some embodiments, including the example embodiment illustrated in FIG. 4, the HPLC-based QCM 50 according to the present general inventive concept includes a radiation detector 522 with one or more radiation probes; in the illustrated example embodiment shown in FIG. 4, the radiation detector 522 includes at least one radiation probe 542. Further, in some embodiments, the HPLC-based QCM 50 includes an UV/VIS detector 502 to test the optical qualities of the sample. In some embodiments, the HPLC-based QCM 50 includes an RI detector 505 to test the radionuclidic identity of the sample.

Figure 5:
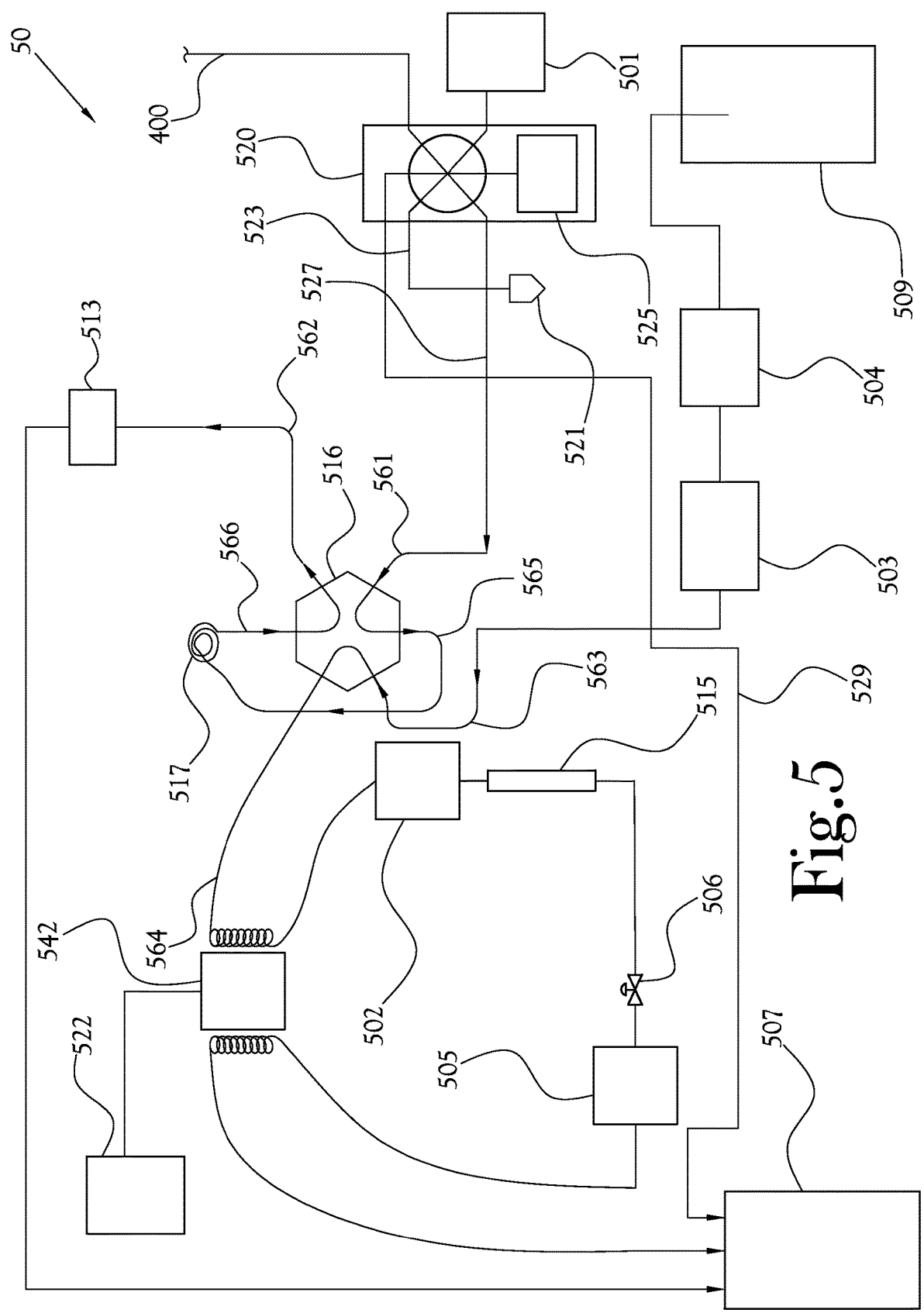
FIG. 5 is a second flow diagram illustration of the example embodiment of an HPLC-based QCM shown in FIG. 4, showing the injection valve in a second state.

In the normal operation of one example embodiment of the present general inventive concept, as illustrated in FIGS. 4 and 5, a sample radiopharmaceutical solution enters the syringe-pump assembly 520 from the quality-control transfer line 400. Within the syringe-pump assembly 520, the sample radiopharmaceutical solution is stored within a syringe 525. Then, a portion of the sample radiopharmaceutical solution is propelled by the syringe 525 or a similar mechanism and thereby is loaded, in a steady, even, and substantially reproducible manner, into a first QCM pathway 527. In some embodiments, the syringe-pump assembly 520 draws water or other solvent, such as LAL reagent water, from a reagent water reservoir 501. The sample radiopharmaceutical solution moves through the first QCM pathway 527 and passes through a first injection valve line 561 to enter the injection valve 516. Another portion of the sample radiopharmaceutical solution within the syringe 525 is directed within the syringe-pump assembly 520 to enter a second QCM pathway 523; this second portion of the sample radiopharmaceutical solution passes through the second QCM pathway 523 into an endotoxin testing sample vessel 521. Any remainder third portion of the sample radiopharmaceutical solution within the syringe 525 is directed within the syringe-pump assembly 520 to enter a third QCM pathway 529, which conveys the remainder third portion of the sample radiopharmaceutical solution to a waste vessel 507.

In some embodiments, in the normal course of conducting quality control tests on the sample radiopharmaceutical solution, an aliquot of the sample radiopharmaceutical solution is tested for endotoxicity. In some embodiments, sample aliquot collected in the test vial 521 is tested for endotoxicity by diluting the sample aliquot and subjecting the diluted sample aliquot to an endotoxicity test. In some embodiments, the endotoxicity test is conducted by an automated endotoxin detector. In some embodiments, the endotoxicity test is conducted by an automated endotoxin spectrophotometer. In some embodiments, the endotoxicity test comprises the use of a kinetic hemocyte lysate-based assay for the detection and quantification of microbial contaminants. In some embodiments, other forms of endotoxicity tests are used.

As illustrated in FIGS. 4 and 5, there are six fluid-carrying lines that lead into or out of the injection valve: the first injection valve line 561, the second injection valve line 562, the third injection valve line 563, the fourth injection valve line 564, the fifth injection valve line 565, the sixth injection valve line 566.

The first injection valve line 561 conveys the sample radiopharmaceutical solution from the syringe-pump assembly 520 into the injection valve 516.

The second injection valve line 562 conveys solution from the injection valve 516 to a pH detector 513. In some embodiments, the pH detector 513 includes a solid state detector. In some embodiments, the pH detector 513 includes an in-line solid state pH detector. After the solution passes through the pH detector 513, the solution is directed to the waste vessel 507.

The third injection valve line 563 conveys to the injection valve 516 mobile phase solvent drawn by the HPLC pump 503 from the mobile phase solvent reservoir 509 through the degasser 504. The fourth injection valve line 564 conveys fluid from the injection valve 516 to the HPLC column 515.

The fifth injection valve line 565 conveys fluid from the injection valve 516 into the fixed-volume fluid loop 517, and the sixth valve line 566 conveys fluid from the fixed-volume fluid loop 517 into the injection valve 516. Thus, three of the injection valve lines 561, 563, and 566 are input lines, and three of the injection valve lines 562, 564, and 565 are output lines.

In various embodiments, the injection valve 516 directs incoming fluid (generally the sample radiopharmaceutical solution or the mobile phase solvent) from an input line to an output line. FIGS. 4 and 5 show the injection valve 516 in two different states. In the first state (also called State A), shown in FIG. 4, the injection valve 516 is positioned such that a channel within the injection valve 516 directs fluid from the first injection valve line 561 to the second injection valve line 562; that is, in State A, sample radiopharmaceutical solution passes from the first QCM pathway 527, through the first injection valve line 561, through the injection valve 516, and then through the second injection valve line 562 to the pH detector 513. In State A, mobile phase solvent from the HPLC pump 503 passes through the third injection valve line 563 into the injection valve 516. Within the injection valve 516, mobile phase solvent from the third injection valve line 563 is directed into the fifth injection valve line 565 and then into the fixed-volume fluid loop 517. The mobile phase solvent within the fixed-volume fluid loop 517 continues through the sixth injection valve line 566 back into the injection valve 516, where the mobile phase solvent is directed into the fourth injection valve line 564 and thereafter conveyed to the HPLC column 515.

During the quality control testing process, at a point where sample radiopharmaceutical solution is flowing from the syringe-pump assembly 520 through the pH detector 501 and through the first injection valve line 561, the injection valve 516 is rotated 60 degrees into the second state (or State B), shown in FIG. 5. In State B, the sample radiopharmaceutical solution passes from the first injection valve line 561, through the injection valve 516, and then into the fifth injection valve line 565; from the fifth injection valve line 565, the sample radiopharmaceutical solution enters the fixed-volume fluid loop 517. As fluid continues to flow while the injection valve 516 is in State B, sample radiopharmaceutical solution flowing through the fixed-volume fluid loop 517 exits the fixed-volume fluid loop 517 and re-enters the injection valve 516 through the sixth injection valve line 566; the sample radiopharmaceutical solution is then directed into the second injection valve line 562, and the sample radiopharmaceutical solution passes through the second injection valve line 562 to the pH detector 513 and the waste vessel 507.

While sample radiopharmaceutical solution is flowing through the fixed-volume fluid loop 517, the injection valve 516 is rotated a second time, so that the injection valve is again in State A (as in FIG. 4). At this point in time, mobile phase solvent from the HPLC pump 503 passes through the third injection valve line 563 and into the injection valve 516; within the injection valve 516, the mobile phase solvent from the third injection valve line 563 is directed into the fifth injection valve line 565. The mobile phase solvent within the fifth injection valve line 565 enters the fixed-volume fluid loop 517, pushing the sample radiopharmaceutical solution within the fixed-volume fluid loop 517 out of the fixed-volume fluid loop 517 and through the sixth injection valve line 566 into the injection valve 516. Within the injection valve 516, the sample radiopharmaceutical solution from the fixed-volume fluid loop 517 is directed into the fourth injection valve line 564. (In some embodiments, the fixed-volume loop 517 has a volume of approximately 20 microliters. However, those of skill in the art will recognize that other volumes the fixed-volume loop 517 are possible and are contemplated by the present invention.)

Conveyed along the fourth injection valve line 564, the sample radiopharmaceutical solution from the fixed-volume fluid loop 517 passes by a radiation probe 542, which is part of or connected to a radiation detector 522. Next, the sample radiopharmaceutical solution passes by or through a UV/VIS detector 502 to test the optical clarity of the sample radiopharmaceutical solution. In some embodiments, the UV/VIS detector 502 comprises a ultra-violet and visible light spectrometer. In some embodiments, the UV/VIS detector 502 comprises a UV spectrophotometer. In some embodiments, the UV/VIS detector 502 comprises a UV spectrophotometer with a deuterium light source. In some embodiments, the UV/VIS detector 502 comprises a UV spectrophotometer with a tungsten-halogen light source. In some embodiments, the UV/VIS detector 502 comprises a UV spectrophotometer like the Smartline UV Detector 2500, manufactured by KNAUER. In some embodiments, the HPLC-based QCM 50 includes a detector comprises a spectrophotometer that detects a range of the electromagnetic spectrum that includes infrared light. In some embodiments, the HPLC-based QCM 50 includes multiple detectors, including, in some embodiments, multiple UV/VIS detectors or, in some embodiments, multiple spectrophotometers or spectrometers.

In some embodiments, the UV/VIS detector 502 tests the sample radiopharmaceutical solution for the presence of residual Krypotofix. Generally, a purified radiopharmaceutical solution will be considered to pass quality control testing for Kryptofix if the residual concentration of Kryptofix in the final product is less than or equal to 50 micrograms per milliliter solution.

In some embodiments, the radiopharmaceutical solution from the fixed-volume fluid loop 517 passes by or through the UV/VIS detector 502 before entering the HPLC column 515, as shown in FIG. 4. In some embodiments, the radiopharmaceutical solution from the fixed-volume fluid loop 517 passes by or through a UV/VIS detector after entering and passing though the HPLC column 515.

In the illustrated example embodiment shown in FIG. 4, after passing by or through the UV/VIS detector 502, the sample radiopharmaceutical solution passes into the HPLC column 515. The HPLC column 515 separates [$^{18}$F]FDG within the sample radiopharmaceutical solution from any other radioactive products or other organic impurities. In this way, the HPLC column 515 assists testing the radiochemical identity of the sample radiopharmaceutical solution—that is, the HPLC column 515 helps to identify the ratio of [$^{18}$F]FDG (or other desired radiopharmaceutical compound) to other radioactive products (such as free F-18 ion and [$^{18}$F]FTAG). The HPLC column 515 separates the [$^{18}$F]FDG from other compounds based on their different retention time, making possible the identification of the [$^{18}$F]FDG based on retention time and allowing other instruments to analyze the [$^{18}$F]FDG separately from other compounds. Thus, in some embodiments, after exiting the HPLC column 515, the sample radiopharmaceutical solution passes through a refractive index detector (RI detector) 505. The RI detector 505 detects, measures and quantifies the presence of compounds as they are eluted from the HPLC column 515. [$^{18}$F]FDG is identified based on its retention time, as are other compounds present in the sample radiopharmaceutical solution. In general, [$^{18}$F]FDG has a slightly shorter retention time compared to FDG that lacks a radioisotope. In some embodiments, the radiochemical purity of the separated [$^{18}$F]FDG within the sample radiopharmaceutical solution is also measured after the elution of the separated [$^{18}$F]FDG within the sample radiopharmaceutical solution from the HPLC column 515.

In many embodiments, the RI detector 505 also measures the residual concentration in the sample radiopharmaceutical solution of solvents such as acetonitrile and ethanol. Generally, a purified radiopharmaceutical solution will be considered to pass quality control testing if the residual concentration of acetonitrile in the sample radiopharmaceutical solution is less than or equal to 400 ppm.

In some embodiments, an HPLC-based QCM 50 according to the present general inventive concept includes a radiation detector 522 with at least one radiation probe 542. As shown in FIGS. 4 and 5, the radiation probe 542 measures the radioactivity of the separated [$^{18}$F]FDG within the sample radiopharmaceutical solution eluted from the HPLC column 515. The radiation probe 542 also measures the radioactivity of other radioactive products (such as free F-18 ion and [$^{18}$F]FTAG) eluted from the HPLC column 515.

Generally, after the sample radiopharmaceutical solution is eluted from the HPLC column 515 and tested for radiochemical identity, radiochemical purity, and the presence of residual impurities, the sample radiopharmaceutical solution is conveyed to the waste vessel 507. In some embodiments, HPLC-based QCM 50 according to the present general inventive concept also includes, on the line carrying the sample radiopharmaceutical solution from the HPLC column 515 to the waste vessel 507, a backpressure valve 506.

The present general inventive concept comprises an HPLC-based quality control system for conducting a number of automated tests on a radiopharmaceutical solution, and in particular on a synthesized and purified radiopharmaceutical solution for use in positron emission tomography. An HPLC-based quality control system according to the present general inventive concept provides a quality control testing system that makes efficient use of sample volume. The present general inventive concept is compatible with and able to test a variety of radioisotopes and radiopharmaceutical compounds. Further, the automated nature of an HPLC-based quality control system according to the present general inventive concept allows for quality control tests to be conducted quickly and with minimal impact on user workflow; the automated system relieves a technician from having to perform a number of the quality control tests. Overall, and especially when used as part of an integrated PET biomarker radiopharmaceutical production system as described above, the present general inventive concept permits a radiopharmaceutical manufacturer to produce product and conduct quality control tests on the product with lower per dose costs.

While the present invention has been illustrated by description of one embodiment, and while the illustrative embodiment has been described in detail, it is not the intention of the applicant to restrict or in any way limit the scope of the appended claims to such detail. Additional modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An integrated radiopharmaceutical production and quality control testing system, the system comprising:
   a cyclotron configured to form a radioisotope in a fluid phase;
   a chemical production module in communication with the cyclotron configured to receive the radioisotope in the fluid phase, the chemical production module configured to form a purified radiopharmaceutical solution including the radioisotope;
   a quality control module in communication with the chemical production module, the quality control module configured to receive from the chemical production module a sample radiopharmaceutical solution of the purified radiopharmaceutical solution including the radioisotope, the quality control module including:
      a pumping mechanism coupled to the chemical production module and configured to receive from the chemical production module the sample radiopharmaceutical solution of the purified radiopharmaceutical solution including the radioisotope, the pumping mechanism configured to separate the sample radiopharmaceutical solution into a first portion, a second portion, and a third portion;
      a valve mechanism in downstream communication with the pumping mechanism and configured to selectively receive at least two of the three portions of the sample radiopharmaceutical solution from the pumping mechanism;
      wherein said valve mechanism comprises a plurality of input and output valve lines;
      wherein said valve mechanism is configured to rotate at a predetermined angle to change configuration from a state A to a state B for selectively directing the at least two of the three portions of the sample radiopharmaceutical solution through different predefined pairs of input and output valve lines;
      a light analyzer in communication with the valve mechanism configured to receive the first portion of the sample radiopharmaceutical solution and to determine the optical clarity of the sample radiopharmaceutical solution from the first portion of the sample radiopharmaceutical solution;
      a high performance liquid chromatography column in communication with the valve mechanism, the high performance liquid chromatography column configured to receive the first portion of the sample radiopharmaceutical solution and to separate the first portion of the sample radiopharmaceutical solution into a number of separated molecularly distinct species, the high performance liquid chromatography column in downstream communication with the light analyzer;
      a mobile phase solvent mechanism in communication with the valve mechanism, the mobile phase solvent mechanism having a mobile phase solvent reservoir configured to store a mobile phase solvent therein to selectively introduce the mobile phase solvent into the high performance liquid chromatography column through the valve mechanism to facilitate separation of the radiopharmaceutical solution into the number of separated molecularly distinct species;
      a refractive index analyzer in downstream communication with the high performance liquid chromatography column, the refractive index analyzer configured to receive the separated molecularly distinct species from the high performance liquid chromatography column and to determine the refractive index of and quantify each of the number of separated molecularly distinct species in the sample radiopharmaceutical solution from the first portion of the sample radiopharmaceutical solution; and
      a radiation probe disposed in the quality control module, the radiation probe in communication with the valve mechanism and in upstream and downstream communication with the high performance liquid chromatography column, the radiation probe configured to measure the radioactivity of the first portion of the sample radiopharmaceutical solution upstream of and before the first portion of the sample radiopharmaceutical solution enters the high performance liquid chromatography column and to measure the radioactivity of each of the number of separated molecularly distinct species in the sample radiopharmaceutical solution from the separated molecularly distinct species in the first portion of the sample radiopharmaceutical solution after the separated molecularly distinct species exit downstream of the high performance liquid chromatography column.

2. The integrated radiopharmaceutical production and quality control testing system of claim 1, wherein:
   the light analyzer comprises an ultraviolet light analyzer and a colorimetric detector, the colorimetric detector configured to determine a visible light spectra of the sample radiopharmaceutical solution from the first portion of the sample radiopharmaceutical solution.

3. The integrated radiopharmaceutical production and quality control testing system of claim 2, wherein:
the colorimetric detector is further configured to determine the clarity of the sample radiopharmaceutical solution from the first portion of the sample radiopharmaceutical solution.

4. The integrated radiopharmaceutical production and quality control testing system of claim 1, further comprising:
an endotoxicity analyzer in communication with the pumping mechanism, the endotoxicity analyzer configured to receive from the pumping mechanism the second portion of the sample radiopharmaceutical solution, the endotoxicity analyzer configured to determine the endotoxicity of the sample radiopharmaceutical solution from the second portion of the sample radiopharmaceutical solution.

5. The integrated radiopharmaceutical production and quality control testing system of claim 4, wherein:
the endotoxicity analyzer implements a kinetic hemocyte lysate-based assay.

6. The integrated radiopharmaceutical production and quality control testing system of claim 1, further comprising:
a pH detector in communication with the valve mechanism and configured to receive the third portion of the sample radiopharmaceutical solution, the pH detector determining the pH of the sample radiopharmaceutical solution from the third portion of the sample radiopharmaceutical solution.

7. The integrated radiopharmaceutical production and quality control testing system of claim 1, wherein:
the purified radiopharmaceutical solution includes a volatile organic contaminant selected from the group consisting of acetonitrile, ethanol, methyl cyanide, and combinations thereof, the refractive index analyzer also configured to measure a residual concentration of at least one said volatile organic contaminant.

8. The integrated radiopharmaceutical production and quality control testing system of claim 1, wherein:
the radioisotope is selected from the group consisting of carbon-11, nitrogen-13, oxygen-15, and fluorine-18.

9. The integrated radiopharmaceutical production and quality control testing system of claim 1, wherein:
the purified radiopharmaceutical solution includes [$^{18}$F]-2-fluoro-2-deoxy-D-glucose as a radiopharmaceutical.

10. The integrated radiopharmaceutical production and quality control testing system of claim 1, wherein:
the radioisotope is selected from the group consisting of carbon-11, nitrogen-13, oxygen-15, and fluorine-18, and
the purified radiopharmaceutical solution includes a volatile organic contaminant selected from the group consisting of acetonitrile, ethanol, methyl cyanide, and combinations thereof.

11. The integrated radiopharmaceutical production and quality control testing system of claim 1, wherein:
the quality control module is configured to determine from the radiation probe at least one of radionuclidic identity, radionuclide purity, radiochemical identity, and radiochemical purity for at least one of the number of separated molecularly distinct species in the sample radiopharmaceutical solution from the first portion of the sample radiopharmaceutical solution.

12. The integrated radiopharmaceutical production and quality control testing system of claim 1, wherein:
the quality control module is configured to quantify from the refractive index analyzer compounds in each of the number of separated molecularly distinct species.

13. The integrated radiopharmaceutical production and quality control testing system of claim 1, wherein:
the quality control module is configured to determine the radioactivity of [$^{18}$F]-2-fluoro-2-deoxy-D-glucose in the separated molecularly distinct species from the radioactivity measured by the radiation probe.

14. The integrated radiopharmaceutical production and quality control testing system of claim 1, wherein:
the quality control module is configured to detect from the light analyzer the presence of potassium organometallic complexes, crown ethers, and Kryptofix 2.2.2 (1,10-diaza-4,7,13,16,21,24-hexaoxabicyclo[8.8.8]hexacosane) in the sample radiopharmaceutical solution from the first portion of the sample radiopharmaceutical solution.

15. The integrated radiopharmaceutical production and quality control testing system of claim 14, wherein:
the quality control module is configured to determine from the radiation probe a ratio of the radioactivity of the separated molecularly distinct species [$^{18}$F]-2-fluoro-2-deoxy-D-glucose to the radioactivity of the sample radiopharmaceutical solution from the first portion of the sample radiopharmaceutical solution.

16. A quality control module for quality control testing of a radiopharmaceutical solution, comprising:
a pumping mechanism configured to receive a sample radiopharmaceutical solution of a purified radiopharmaceutical solution including a radioisotope, the pumping mechanism configured to separate the radiopharmaceutical solution into a first portion, a second portion, and a third portion;
a valve mechanism in downstream communication with the pumping mechanism and configured to selectively receive at least two of the three portions of the sample radiopharmaceutical solution from the pumping mechanism;
wherein said valve mechanism comprises a plurality of input and output valve lines; and
wherein said valve mechanism is configured to rotate at a predetermined angle to change configuration from a state A to a state B for selectively directing the at least two of the three portions of the sample radiopharmaceutical solution through different predefined pairs of input and output valve lines;
a light analyzer in communication with the valve mechanism configured to receive the first portion of the sample radiopharmaceutical solution and to determine the optical clarity of the first portion of the sample radiopharmaceutical solution;
a high performance liquid chromatography column in communication with the valve mechanism configured to receive the first portion of the sample radiopharmaceutical solution and to separate the first portion of the sample radiopharmaceutical solution into a number of separated molecularly distinct species, the high performance liquid chromatography column in downstream communication with the light analyzer;
a mobile phase solvent mechanism in communication with the valve mechanism, the mobile phase solvent mechanism having a mobile phase solvent reservoir configured to store a mobile phase solvent therein to selectively introduce the mobile phase solvent into the high performance liquid chromatography column through the valve mechanism to facilitate separation of the radiopharmaceutical solution into the number of separated molecularly distinct species;

a refractive index analyzer in downstream communication with the high performance liquid chromatography column, the refractive index analyzer configured to receive the separated molecularly distinct species from the high performance liquid chromatography column and to determine the refractive index of and quantify each of the number of separated molecularly distinct species in the sample radiopharmaceutical solution from the first portion of the sample radiopharmaceutical solution; and a radiation probe disposed in the quality control module, the radiation probe in communication with the valve mechanism and in upstream and downstream communication with the high performance liquid chromatography column, the radiation probe configured to measure the radioactivity of the first portion of the sample radiopharmaceutical solution upstream of and before the first portion of the sample radiopharmaceutical solution enters the high performance liquid chromatography column and to measure the radioactivity of each of the number of separated molecularly distinct species in the sample radiopharmaceutical solution from the separated molecularly distinct species in the first portion of the sample radiopharmaceutical solution after the separated molecularly distinct species exit downstream of the high performance liquid chromatography column;

wherein when the valve mechanism is in the state A, the first portion of the sample radiopharmaceutical solution is directed to the high performance liquid chromatography column; and wherein when the valve mechanism is in the state B the third portion of the sample radiopharmaceutical solution is directed to a pH detector in communication with the valve mechanism configured to receive the third portion of the sample radiopharmaceutical solution, the pH detector determining the pH of the sample radiopharmaceutical solution from the third portion of the sample radiopharmaceutical solution.

17. The quality control module for quality control testing of a radiopharmaceutical solution of claim 16, wherein the light analyzer comprises:

an ultraviolet light analyzer and a colorimetric detector, the colorimetric detector configured to determine a visible light spectra of the sample radiopharmaceutical solution from the first portion of the sample radiopharmaceutical solution.

18. The quality control module for quality control testing of a radiopharmaceutical solution of claim 16, further comprising:

an endotoxicity analyzer in communication with the pumping mechanism, the endotoxicity analyzer configured to receive from the pumping mechanism the second portion of the sample radiopharmaceutical solution, the endotoxicity analyzer configured to determine the endotoxicity of the sample radiopharmaceutical solution from the second portion of the sample radiopharmaceutical solution.

19. The quality control module for quality control testing of a radiopharmaceutical solution of claim 16, wherein:

the purified radiopharmaceutical solution includes [$^{18}$F]-2-fluoro-2-deoxy-D-glucose as a radiopharmaceutical.

20. The quality control module for quality control testing of a radiopharmaceutical solution of claim 16, wherein:

the radioisotope is selected from the group consisting of carbon-11, nitrogen-13, oxygen-15, and fluorine-18, and the purified radiopharmaceutical solution includes a volatile organic contaminant selected from the group consisting of acetonitrile, ethanol, methyl cyanide, and combinations thereof.

21. The quality control module for quality control testing of a radiopharmaceutical solution of claim 16, wherein:

the quality control module is configured to determine from the radiation probe at least one of radionuclidic identity, radionuclide purity, radiochemical identity, and radiochemical purity for at least one of the number of separated molecularly distinct species in the sample radiopharmaceutical solution from the first portion of the sample radiopharmaceutical solution, and the quality control module is configured to quantify from the refractive index analyzer compounds in each of the number of separated molecularly distinct species.

22. The quality control module for quality control testing of a radiopharmaceutical solution of claim 16, wherein:

the quality control module is configured to determine the radioactivity of [$^{18}$F]-2-fluoro-2-deoxy-D-glucose in the separated molecularly distinct species from the radioactivity measured by the radiation probe.

23. The quality control module for quality control testing of a radiopharmaceutical solution of claim 16, wherein:

the quality control module is configured to detect from the light analyzer the presence of potassium organometallic complexes, crown ethers, and Kryptofix 2.2.2 (1,10-diaza-4,7,13,16,21,24-hexaoxabicyclo[8.8.8]hexacosane) in the sample radiopharmaceutical solution from the first portion of the sample radiopharmaceutical solution, and the quality control module is configured to determine from the radiation probe a ratio of the radioactivity of the separated molecularly distinct species [$^{18}$F]-2-fluoro-2-deoxy-D-glucose to the radioactivity of the sample radiopharmaceutical solution from the first portion of the sample radiopharmaceutical solution.

24. A quality control module for quality control testing of a radiopharmaceutical solution, comprising:

a pumping mechanism configured to receive a sample radiopharmaceutical solution of a purified radiopharmaceutical solution including a radioisotope, the pumping mechanism configured to separate the sample radiopharmaceutical solution into a plurality of portions;

a valve mechanism in downstream communication with the pumping mechanism and configured to receive selected ones of the plurality of portions of the sample radiopharmaceutical solution from the pumping mechanism;

wherein said valve mechanism comprises a plurality of input and output valve lines;

wherein said valve mechanism is configured to rotate at a predetermined angle to change configuration from a state A to a state B for selectively directing the selected ones of the plurality of portions of the sample radiopharmaceutical solution through different predefined pairs of input and output valve lines;

a light analyzer in communication with the valve mechanism configured to receive a first portion of the plurality of portions of the sample radiopharmaceutical solution and to determine the optical clarity of the first portion of the sample radiopharmaceutical solution;

a high performance liquid chromatography column in communication with the valve mechanism configured to receive the first portion of the plurality of portions of the sample radiopharmaceutical solution and to separate the first portion of the plurality of portions of the sample radiopharmaceutical solution into a number of separated molecularly distinct species, the high performance liquid chromatography column in downstream communication with the light analyzer;

a mobile phase solvent mechanism in communication with the valve mechanism, the mobile phase solvent mechanism having a mobile phase solvent reservoir configured to store a mobile phase solvent therein to selectively introduce the mobile phase solvent into the high performance liquid chromatography column through the valve mechanism to facilitate separation of the radiopharmaceutical solution into the number of separated molecularly distinct species;

a refractive index analyzer in downstream communication with the high performance liquid chromatography column, the refractive index analyzer configured to receive the separated molecularly distinct species from the high performance liquid chromatography column and to determine the refractive index of and quantify each of the number of separated molecularly distinct species in the sample radiopharmaceutical solution from the first portion of the plurality of portions of the sample radiopharmaceutical solution; and a radiation probe disposed in the quality control module, the radiation probe in communication with the valve mechanism and in upstream and downstream communication with the high performance liquid chromatography column, the radiation probe configured to measure the radioactivity of the first portion of the plurality of portions of the sample radiopharmaceutical solution upstream of and before the first portion of the plurality of portions of the sample radiopharmaceutical solution enters the high performance liquid chromatography column and to measure the radioactivity of each of the number of separated molecularly distinct species in the sample radiopharmaceutical solution from the separated molecularly distinct species in the first portion of the plurality of portions of the sample radiopharmaceutical solution after the separated molecularly distinct species exit downstream of the high performance liquid chromatography column.

25. A quality control module for quality control testing of a radiopharmaceutical solution, comprising:

a pump assembly adapted to be coupled to a quality-control line from a radiopharmaceutical production system, the pump assembly configured to receive a sample radiopharmaceutical solution of a purified radiopharmaceutical solution including a radioisotope, the pump assembly configured to separate the sample radiopharmaceutical solution into a first portion, a second portion, and a third portion;

at least one pathway coupled to the pump assembly, the pump assembly configured to selectively pump a portion of the sample radiopharmaceutical solution through the at least one pathway to selectively perform at least one test on the sample radiopharmaceutical solution;

a valve mechanism in downstream communication with the pump assembly, the valve mechanism configured to selectively receive and direct at least two of the three portions of the sample radiopharmaceutical solution from the pump assembly, the valve mechanism comprising:

a plurality of valve fluid pathways defined therein;

wherein the valve mechanism is configured to rotate at a predetermined angle to change configuration from a state A to a state B; and at least two pairs of inlets and outlets selectively formed by the plurality of valve fluid pathways depending on selective positioning of the valve mechanism, the quality control module having a plurality of valve lines in selective communication with the valve mechanism, the valve mechanism being selectively positioned to align at least two pairs of inlets and outlets to a corresponding select two pairs of valve lines, each pair of select valve lines directing one of the three portions of the sample radiopharmaceutical solution into a selective predetermined processing flow path;

a light analyzer in communication with the valve mechanism configured to receive the first portion of the sample radiopharmaceutical solution and to determine the optical clarity of the first portion of the sample radiopharmaceutical solution;

a high performance liquid chromatography (HPLC) column in communication with the valve mechanism configured to receive the first portion of the sample radiopharmaceutical solution and to separate the first portion of the sample radiopharmaceutical solution into a number of separated molecularly distinct species, the HPLC column in downstream communication with the light analyzer;

a mobile phase solvent mechanism in communication with the valve mechanism, the mobile phase solvent mechanism including:

a mobile phase solvent reservoir configured to store a mobile phase solvent therein;

a degasser in downstream communication with the mobile phase solvent reservoir, the degasser configured to remove dissolved gases in the mobile phase solvent; and a HPLC pump in downstream communication with the degasser, the HPLC pump configured to selectively draw the mobile phase solvent through the degasser from the mobile phase solvent reservoir and selectively introduce the mobile phase solvent into the HPLC column through the valve mechanism to facilitate separation of the sample radiopharmaceutical solution into the number of separated molecularly distinct species, the valve mechanism configured to also selectively receive and direct the mobile phase solvent through a pair of select valve lines at each state of the valve mechanism and directing the same into a selective predetermined processing flow path towards the HPLC column;

a refractive index analyzer in downstream communication with the HPLC column, the refractive index analyzer configured to receive the separated molecularly distinct species from the HPLC column and to determine the refractive index of and quantify each of the number of separated molecularly distinct species in the sample radiopharmaceutical solution from the first portion of the sample radiopharmaceutical solution; and a radiation probe disposed in the quality control module, the radiation probe in communication with the valve mechanism and in upstream and downstream communication with the HPLC column, the radiation probe configured to measure the radioactivity of the first portion of the sample radiopharmaceutical solution upstream of and before the first portion of the sample radiopharmaceutical solution enters the HPLC column and to measure the radioactivity of each of the number of separated molecularly distinct species in the sample radiopharmaceutical solution from the separated molecularly distinct species in the first portion of the sample radiopharmaceutical solution after the separated molecularly distinct species exit downstream of the HPLC column;

wherein when the valve mechanism is in the state A, the first portion of the sample radiopharmaceutical solution is directed to the HPLC column; and wherein when the valve mechanism is in the state B, the third portion of the sample radiopharmaceutical solution is directed to a pH detector in communication with the valve mechanism configured to receive the third portion of the sample radiopharmaceutical solution, the pH detector determining the pH of the sample radiopharmaceutical solution from the third portion of the sample radiopharmaceutical solution.

26. The quality control module for quality control testing of a radiopharmaceutical solution of claim 25, wherein the plurality of valve lines comprises:

a first valve line communicating with the pump assembly, the first valve line defining a first pathway of the at least one pathway of the pump assembly;

a second valve line communicating with the pH detector;

a third valve line communicating with the HPLC pump;

a fourth valve line communicating with the HPLC column;

a fifth valve line communicating with an input of a fixed volume loop; and a sixth valve line communicating with an output of the fixed volume loop.

27. The quality control module for quality control testing of a radiopharmaceutical solution of claim 26, wherein:

a first position of the valve mechanism comprises:
the first valve line and the second valve line forming a first inlet and outlet pair of the at least two pairs of inlets and outlets directing flow of the sample radiopharmaceutical solution between the pump assembly and the pH detector;
the third valve line and the fifth valve line forming a second inlet and outlet pair of the at least two pairs of inlets and outlets directing flow of the mobile phase solvent between the HPLC pump and the fixed volume loop; and
the fourth valve line and the sixth valve line forming a third inlet and outlet pair of the at least two pairs of inlets and outlets directing flow of the mobile phase solvent between the fixed volume loop and the HPLC column.

28. The quality control module for quality control testing of a radiopharmaceutical solution of claim 27, wherein:

a second position of the valve mechanism comprises:
the first valve line and the fifth valve line forming a fourth inlet and outlet pair of the at least two pairs of inlets and outlets directing flow of the sample radiopharmaceutical solution between the pump assembly and the fixed volume loop; and
the second valve line and the sixth valve line forming a fifth inlet and outlet pair of the at least two pairs of inlets and outlets directing flow of the sample radiopharmaceutical solution between the fixed volume loop and the pH detector.

29. The quality control module for quality control testing of a radiopharmaceutical solution of claim 28, wherein:

the third valve line and the fourth valve line form a sixth inlet and outlet pair of the at least two pairs of inlets and outlets directing flow of the mobile phase solvent between the HPLC pump and the HPLC column.

30. The quality control module for quality control testing of a radiopharmaceutical solution of claim 28, wherein:

selective positioning of the valve mechanism back and forth between the first position and the second position switches the outlet from the first inlet and outlet pair to the outlet of the fifth inlet and outlet pair to thereby selectively introduce one of the portions of the sample radiopharmaceutical solution in a predetermined sequence through the pH detector.

31. The quality control module for quality control testing of a radiopharmaceutical solution of claim 28, wherein:

selective positioning of the valve mechanism between the first position and the second position switches the outlet from the second inlet and outlet pair to the outlet of the fourth inlet and outlet pair to thereby selectively accumulate a fixed volume of a portion of the sample radiopharmaceutical solution and facilitate fluid transfer of the accumulated fixed volume portion towards the HPLC column with assistance from the mobile phase solvent.

32. The quality control module for quality control testing of a radiopharmaceutical solution of claim 25, wherein:

the light analyzer comprises an ultraviolet light analyzer.

33. The quality control module for quality control testing of a radiopharmaceutical solution of claim 32, further comprising:

a colorimetric detector, the colorimetric detector configured to determine a visible light spectra of the sample radiopharmaceutical solution from the first portion of the sample radiopharmaceutical solution.

34. The quality control module for quality control testing of a radiopharmaceutical solution of claim 25, further comprising:

an endotoxicity analyzer in communication with the pump assembly, a second pathway of the at least one pathway of the pump assembly facilitating the communication between the endotoxicity analyzer and the pump assembly, the endotoxicity analyzer configured to receive from the pump assembly the second portion of the sample radiopharmaceutical solution, the endotoxicity analyzer configured to determine the endotoxicity of the second portion of the sample radiopharmaceutical solution.

* * * * *